United States Patent [19]
Skilling

[11] Patent Number: 5,910,655
[45] Date of Patent: Jun. 8, 1999

[54] REDUCING INTERFERENCES IN ELEMENTAL MASS SPECTROMETERS

[75] Inventor: John Skilling, Cambridge, United Kingdom

[73] Assignee: MaxEnt Solutions Ltd., Cambridge, United Kingdom

[21] Appl. No.: 08/913,012

[22] PCT Filed: Jan. 3, 1997

[86] PCT No.: PCT/GB97/00016

§ 371 Date: Sep. 4, 1997

§ 102(e) Date: Sep. 4, 1997

[87] PCT Pub. No.: WO97/25736

PCT Pub. Date: Jul. 17, 1997

[30] Foreign Application Priority Data

Jan. 5, 1996 [GB] United Kingdom .................. 9600198

[51] Int. Cl.$^6$ .............................. H01J 49/00; B01D 59/44
[52] U.S. Cl. ............................................. 250/281; 250/282
[58] Field of Search ....................................... 250/282, 281

[56] References Cited

U.S. PATENT DOCUMENTS

| | | | |
|---|---|---|---|
| 5,300,771 | 4/1994 | Labowsky | 250/282 |
| 5,331,158 | 7/1994 | Dowell | 250/282 |
| 5,416,750 | 5/1995 | Doyen et al. | 367/73 |
| 5,539,704 | 7/1996 | Doyen et al. | 367/73 |
| 5,581,080 | 12/1996 | Fenn et al. | 250/282 |
| 5,686,726 | 11/1997 | Fenn et al. | 250/282 |

OTHER PUBLICATIONS

D.M. Templeton et al "Applications in Plasma Source Mass Spectrometry", pp. 101–109, Ed. Holland, Pub: Royal Soc. Chem., UK, 1991.

Schecter, "Anal. Chem.", 1996, vol. 68, pp. 170–175.

Bretthorst, "Maximum–Entropy and Bayesian Methods in Science and Engineering", vol. 1, 1988, pp. 75–145.

Sibisi et al "Nature", 1984, vol. 311, pp. 446–447.

Sibisi "Nature", 1983, vol. 301, pp. 134–136.

Lave et al, "J. Mag. Resonan.", 1985, vol. 62, pp. 437–452.

Casella "Chemometrics and Intell. Lab. Systems", vol. 16, pp. 107–125.

Rhode et al "Spectroscopy Letters", 1993, vol. 26 (6), pp. 1085–1102.

Hammond et al "Nuclear Instrum. Meth. in Phys. Res.", 1993, vol. A334, pp. 543–550.

Skilling "Maximum–Entropy and Bayesian Methods in Science and Engineering", vol. 1, 1988, pp. 173–187.

Skilling "Maximum–Entropy and Bayesian Methods in Science and Engineering", vol. 2, 1988, pp. 127–145.

Jaynes, "Maximum–Entropy and Bayesian Methods in Science and Engineering" vol. 1, 1988, pp.–25–29.

*Primary Examiner*—Bruce Anderson
*Attorney, Agent, or Firm*—Alix, Yale & Ristas, LLP

[57] ABSTRACT

The accuracy of the elemental analysis of a sample by mass spectrometry is enhanced by providing plural estimates of the likely mass spectrum of the sample. These estimates are compared with experimentally obtained spectra to generate trial sets of possible compositions of the sample. The generated trial sets are subsequently employed to obtain mean values for the amount of each constituent of the sample.

20 Claims, 6 Drawing Sheets

REDUCING INTERFERENCES IN ELEMENTAL MASS SPECTROMETERS

CROSS-REFERENCE TO RELATED APPLICATIONS

This is the national stage of International Application No. PCT/GB97/00016 filed Jan. 3, 1997.

This invention relates to mass spectrometers and methods of operation thereof. It is particularly applicable to mass spectrometers used for elemental analysis, especially those employing a plasma ion source such as an inductively coupled plasma (ICP) or a microwave-induced plasma (MIP) source. Such instruments typically use a quadrupole mass filter but magnetic-sector mass filters are also used. The invention is applicable to both types.

Mass spectrometers are used to analyse a sample by ionising the sample and separating the ions formed according to their mass-to-charge ratios. Different ionisation techniques are used depending on the different types of sample to be analysed. For elemental analysis, plasma sources are particularly valuable as they generally have low background noise and high sensitivity due in part to the very high source temperatures. However, plasma sources do have some disadvantages. In particular, interferences may occur, which may be due to isotopes of two or more different elements having approximately the same mass, from charged molecular or polyatomic species for example $ArO^+$, $Ar_2^+$ or oxide ions, or from doubly charged species appearing at the same mass-to-charge ratio as a singly charged ion.

One field in which this problem is particularly acute is elemental analysis, particularly of elements such as the Rare Earth Elements (REE) or the transition metal elements. [See e.g. "Applications of Inductively Coupled Plasma Mass Spectrometry" Date A. R. and Gray A. L., (1989) Pub. Blackie and Son, Glasgow, UK.] As discussed therein, many techniques have been developed for avoiding interferences, such as water-cooling the spray chamber in which the sample is nebulized, or altering the composition of the plasma gas. Furthermore, an energy- and mass- filtering method for reducing isobaric interferences in an ICP mass spectrometer has been proposed in WO94/07257.

In addition to changing the hardware parameters, it has been proposed to reduce the effect of interferences by using mathematical techniques to separate out the interference peaks.

Templeton et al ["Applications of Plasma Source Mass Spectrometry" (1991) eds. Holland, Eaton, Pub Royal Soc. Chemistry, UK; pp 101–109 *Multivariate Analysis of ICP Mass Spectra: Determination of Nickel and Iron in Body Fluids*"] propose a method based on Principal Components Analysis (PCA). PCA is a multivariate technique that relies on data reduction and remodelling to derive the minimum number of components necessary to account adequately for a complex system. Templeton et al postulate that the series of factors derived from the spectra by PCA gives an indication of the number of significant components in the system and implicitly the number of interfering components in the spectra. However, in actuality the spectrum may contain interferences to which PCA may be blind so that this approach is fundamentally flawed.

Various other mathematical or statistical techniques have also been proposed for data analysis in different branches of mass spectrometry. DoLago et al [Computers Chem. (1991) Vol.15(2) pp 149–155] propose the interpretation of molecular mass spectra by a simplex method, comparing actual data obtained with calculated isotopic patterns. Mun et al [Anal. Chem. (1977) Vol. 49(12) pp 1723–6] use a library-based technique, comparing the characteristic isotope patterns of Chlorine or Bromine in GC/MS spectra to analyse molecular and fragment ions. Jurasek et al [Mikrochimica Acta (1993) Vol. 110 pp 133–142] also use a similar technique. Although statistical in nature, these latter papers address the different problem of attempting to reconstruct a molecular formula that will fit the observed isotopic mass distribution of an unfragmented molecule. Such work is not fully probabilistic because the question of the intrinsic plausibility of different chemical formulae has not yet been rigorously addressed. In elemental analysis, by contrast, the aim is (to a first approximation) to analyse fragmented molecules in terms of separated atoms, whether or not those elements have the integer ratios that would derive from a single molecular species.

Another approach which has been applied to scientific data analysis is that of Bayesian analysis, which is known to be the only way of reasoning consistently whenever complete certainty is lacking. The Bayesian approach is probabilistic and may be illustrated by considering an instrument, for example a mass spectrometer, which has provided us with some data D. We wish to estimate C, which is the composition of the sample being observed. Any particular composition C induces a mass spectrum M, which consists of data counts observed at different values of mass-to-charge ratio, in accordance with known principles. It is this mass spectrum M which is observed through the instrument. Assuming that we know the instrumental responsivity of the instrument, which we will define as the probabilistic distribution of data counts that would have been observed had the instrument been given any particular calibration input, we can write this "instrumental responsivity" as $$\text{prob}(D \text{ given } M) = p_M(D)$$

or equivalently (because C induces M) as $$\text{prob}(C \text{ given } M) = p_C(D)$$

However, the information we want to know is $$\text{prob}(C \text{ given } D) = p_D(C)$$

These two probabilities are related by Bayes' Theorem.

$$p_D(C) \alpha p(C) p_C(D)$$

where (in standard technical nomenclature) p(C) is known as the prior probability distribution or "prior" for short; $p_c(D)$ is known as the likelihood (or "instrumental responsivity" in our terminology); and $p_D(C)$ is known as the posterior probability distribution, or "posterior" for short, which is the quantity that we want to evaluate. It contains the entire range of compositions that remain plausible in light of the data. As such it gives us error bars as well as an average or "best" single composition. (For a discussion of Bayes' Theorem see Chapter 8 of "The Advanced Theory of Statistics" by M. Kendall and A. Stuart, published by Charles Griffin & Co., London).

Using a Bayesian analysis, therefore, a prior probability distribution p(D) must be assigned before an answer for the posterior can be obtained. This prior must be assigned without reference to the data. The Bayesian approach allows all data to be used fully and consistently in the analysis.

Although other probability distributions may also be used, one well-known Bayesian technique is Maximum Entropy analysis, in which the entropy of the system being studied is used to define the prior probability distribution. A branch of mass spectrometry in which Maximum Entropy has been used is electrospray mass spectrometry (ESMS), which involves the ionisation of complex biological molecules such as proteins by electrospraying. Ions are formed which typically occur with mass-to-charge ratio (M+zH)/z, where M is the molecular mass of the protein, H is the mass of the proton and z is the number of charges on the ion. A series of these ions is formed, each being represented in the mass spectrum by a peak, with a range of z from around 10–20 for a 15 kDa protein. The mass spectrum in this example will therefore be represented by a series of peaks at mass-to-charge ratios (M+10H)/10, (M+11H)/11, (M+12H)/12, etc. The problem in ESMS is to calculate the unknown M and z from this series of peaks.

Ferrige et al [Rapid Comm. in Mass Spectrom. (1992) Vol. 6 pp 707–711] propose the use of Maximum Entropy techniques to deconvolute the electrospray spectra. As discussed, this technique approaches spectral analysis from a Bayesian perspective. However, ESMS spectra consist of series of peaks representing the same protein with successively increasing values of z, so that the same information is present in each peak. A probabilistic approach is therefore well suited to solving the ESMS problem because all of this seemingly redundant data is utilised and the resolution is thereby enhanced in comparison with non-probabilistic methods. However, the repetitive nature of ESMS spectra is quite different from the overlapping spectra obtained in Elemental Analysis which form the problem of the present invention.

It is an objective of the present invention to provide a method for the elemental analysis of a sample by mass spectrometry which overcomes the problem of interferences. It is a further objective of the present invention to provide apparatus for carrying out such a method.

In accordance with the above-mentioned objectives, the invention provides a method of determining the elemental composition of a sample by mass spectrometry comprising the steps of:

1. introducing the sample to be analysed into the ionisation region of a mass spectrometer, the instrumental responsivity of which is known;
2. ionising the said sample so as to produce ions characteristic of the elements present therein;
3. mass analysing and detecting the said ions so as to obtain an experimental spectrum consisting of data counts observed at different values of mass-to-charge ratio characterised in that the method further comprises the steps of:

a. generating a list of possible constituents of the sample, each said constituent having a known isotope ratio pattern;
b. assigning a prior probability distribution to the said list of possible constituents;
c. defining a set of trial compositions corresponding to the results of steps a and b;
d. using the isotope ratio patterns together with the said instrumental responsivity to define a trial mass spectrum corresponding to each said trial composition;
e. defining a posterior probability distribution by using probability calculus to compare the said trial mass spectra and the said experimental mass spectrum;
f. generating a number of trial sets of possible compositions of the sample with their associated likelihood, which said trial sets are consistent with the said posterior probability distribution; and
g. using the said trial sets and associated likelihoods to obtain mean values for the amount of each said constituent of the sample, together with corresponding associated uncertainties.

Preferably, step a above involves the step of obtaining from the human operator of the mass spectrometer an estimate of the likely constituents of the sample. Further preferably, this involves displaying a menu of possible elements and/or species and allowing the operator to select the constituents which he or she estimates are present. Alternatively, however, this information may be obtained automatically.

Advantageously, the trial sets generated in step f above are generated using Gibbs sampling.

Preferably, the method includes the step of allowing the operator of the mass spectrometer to enter a revised estimate of the likely constituents depending on the result of the first or a prior calculation.

According to a further aspect, the invention comprises a mass spectrometer operated according to the above method.

Preferred embodiments of the invention will now be described in greater detail with reference to FIGS. 1–6 in which.

Figure 1:
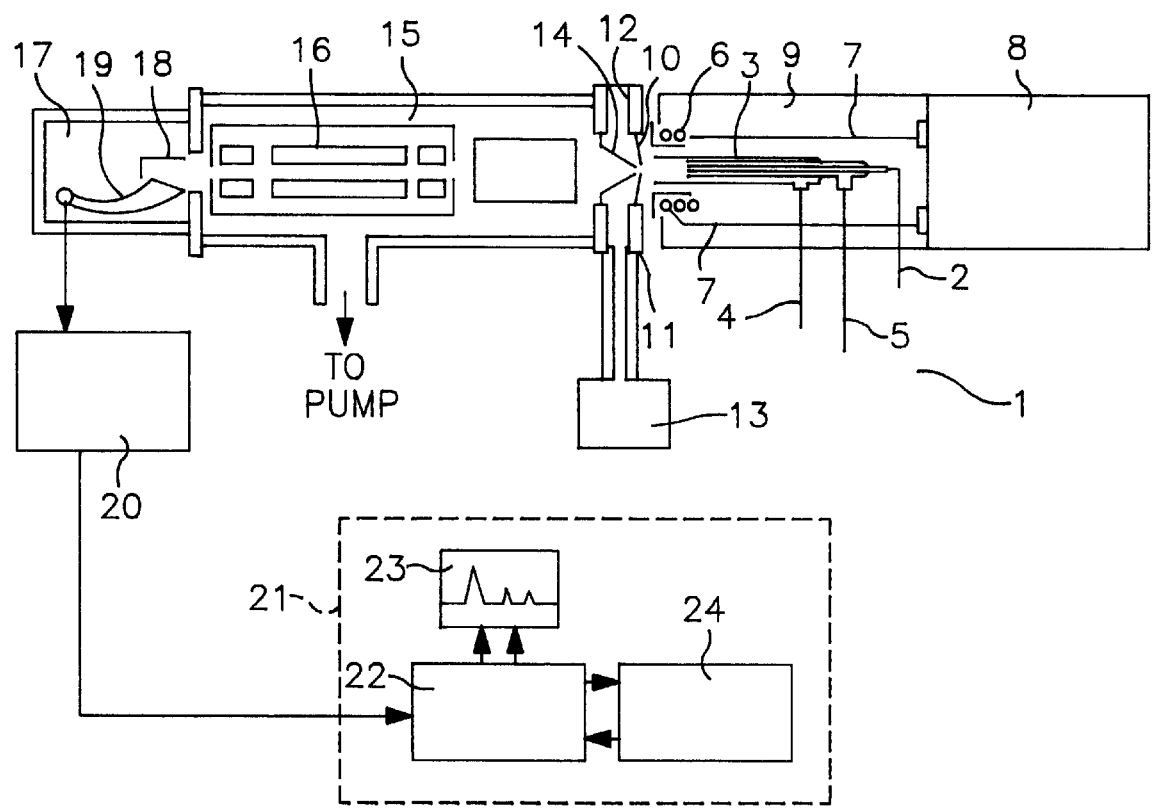
FIG. 1 is a schematic diagram of a conventional ICP mass spectrometer suitable for use with the invention.

A typical configuration of a plasma mass spectrometer, in this case an ICP mass spectrometer, is shown in FIG. 1. The mass spectrometer, indicated generally as 1, comprises means 2 for introducing a sample into a conventional plasma torch 3. Sample preparation means are not shown but may typically comprise a pneumatic nebulizer or other suitable means. Controlled flows 4 5 of inert gas, (typically argon) are supplied to the torch, and radio-frequency electrical means 6 7 8 are provided to generate an inductively-coupled plasma in the gas substantially at atmospheric pressure. In this way an ICP is formed at the end of torch. As discussed, the torch is provided in a region 9 of the mass spectrometer which is substantially at atmospheric pressure. Bounding this region and disposed adjacent to the end of the torch is a nozzle-skimmer interface comprising an orificed sampling cone 10 mounted on a cooled flange 11. The sampling cone forms one boundary of a second region 12 of the mass spectrometer, which is typically maintained substantially below atmospheric pressure (typically 0.01–10 Torr) by a vacuum pump 13. This second region is further bounded by an orificed skimmer cone 14. Beyond the cone is disposed a third, region 15 which is evacuated by a diffusion pump (not shown).

Mass filtering and ion detection means are provided in this case by a quadrupole mass filter 16, disposed in the evacuated region, and an ion detector 17 comprising a converter electrode 18 and an electron multiplier 19. The signal from the multiplier is amplified by an amplifier 20 which in turn feeds a computer 21 typically having a processor 22, a display unit 23 (e.g. a VDU) and data input means 24 (e.g. a keyboard). In this way, an operator may respond to information shown on the display to enter various parameters using the keyboard. Control means (not shown) controlled by the computer also govern the functioning of the various other components of the mass spectrometer.

The mass spectrometer thus described is conventional, and a similar mass spectrometer is described in PCT publication number WO94/07257. Further, as explained, a magnetic sector analyser may be substituted for the quadrupole mass filter.

In operation, the mass spectrometer according to the invention functions as follows. A sample is introduced into the plasma torch 3 by sample introduction means 2. The inductively-coupled plasma at the end of the torch 3 ionises the sample, at least some of these ions passing through orifices in sampling cone 10 and skimmer cone 14 and eventually into the mass filter 16. The voltages applied to the rods of the quadrupole mass filter are altered in the conventional way so as to allow ions of different mass-to-charge ratios to be detected by detector 17. In this way a spectrum is built up which gives the ion signal obtained at a range of different mass-to-charge ratios.

In order to determine the probable composition of the sample from the experimental mass spectrum obtained, firstly a list of the likely constituents of the sample is generated. Preferably, this information is obtained from the operator or operators of the mass spectrometer. In practice this may be achieved, for example, by displaying a menu of possible constituents on display unit 23 and allowing the operator to select from the menu using a data input means such as keyboard 24. It is possible however that the information about the likely content of the sample be entered automatically, for example by the use of bar codes or other such information on a sample container (not shown). It is also possible that the said information be generated automatically by computer 21.

The mass spectrometer then operates according to the method described above to calculate mean values for the amount of each constituent present, together with associated uncertainties.

As described in Chapter 15 of "The Advanced Theory of Statistics" by M. Kendall and A. Stuart, published by Charles Griffin & Co., London, when a trial mass spectrum M is compared to the experimental data counts D in the presence of a normally distributed standard deviation uncertainty σ, the misfit likelihood factor is $$p_M(D) = \prod_k (2\pi\sigma_k^2)^{(-1/2)} \exp\left(\frac{-(M_k - D_k)^2}{2\sigma_k^2}\right)$$

It is this misfit likelihood factor that is used in the comparison of step (e) above. Gibbs sampling, which is preferably used to generate the trial sets of step (f) above, is described in Chapter 11, section 3 of "Bayesian Data Analysis" by A. Gelman et al, published by Chapman & Hall, London, 1995.

Figure 2:
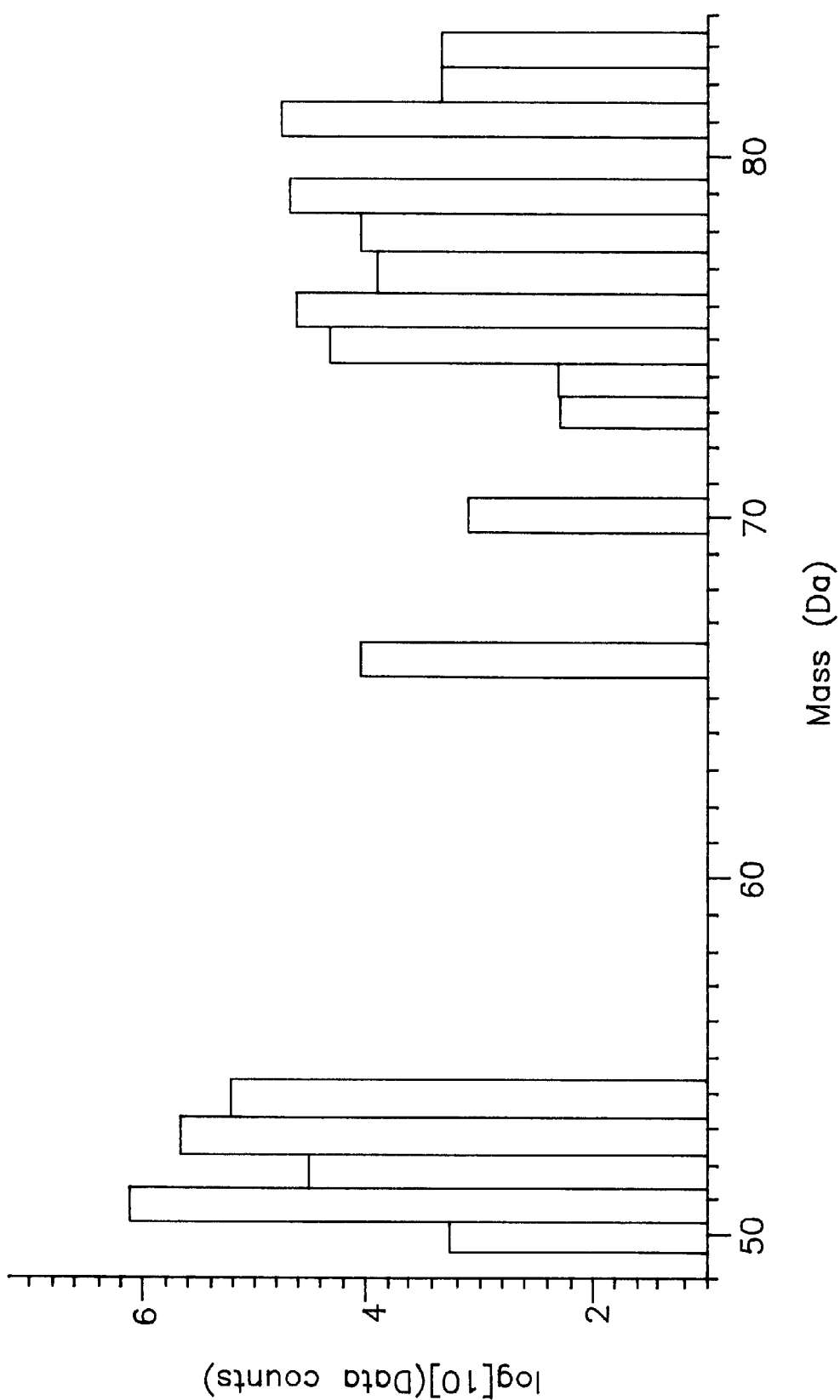
FIG. 2 shows an example of an experimental spectrum.

FIGS. 2–6 show examples of the results of the method according to the present invention. FIG. 2 shows an experimental mass spectrum obtained from a particular sample. The y-axis represents the data counts obtained on a logarithmic scale, while the x-axis represents the mass in Daltons. Note that the x-axis in this case represents mass rather than mass-to-charge ratio—they are equivalent in this particular case since all species are singly charged. Blank columns in FIG. 2 correspond to masses which were not actually monitored.

Figure 3:
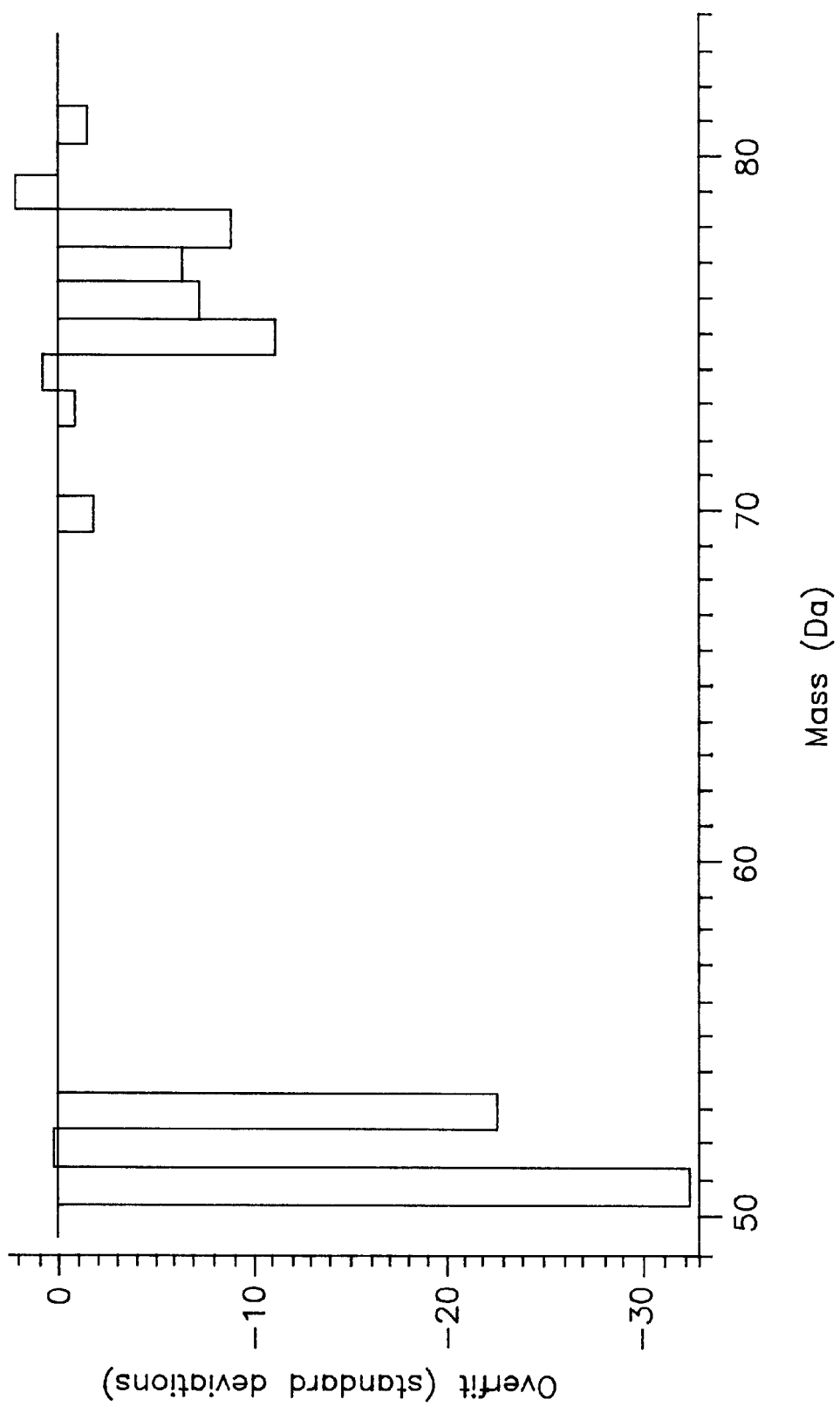
FIGS. 3, 4 and 5 are examples of overfit plots obtained using the method of the invention.
Figure 4:
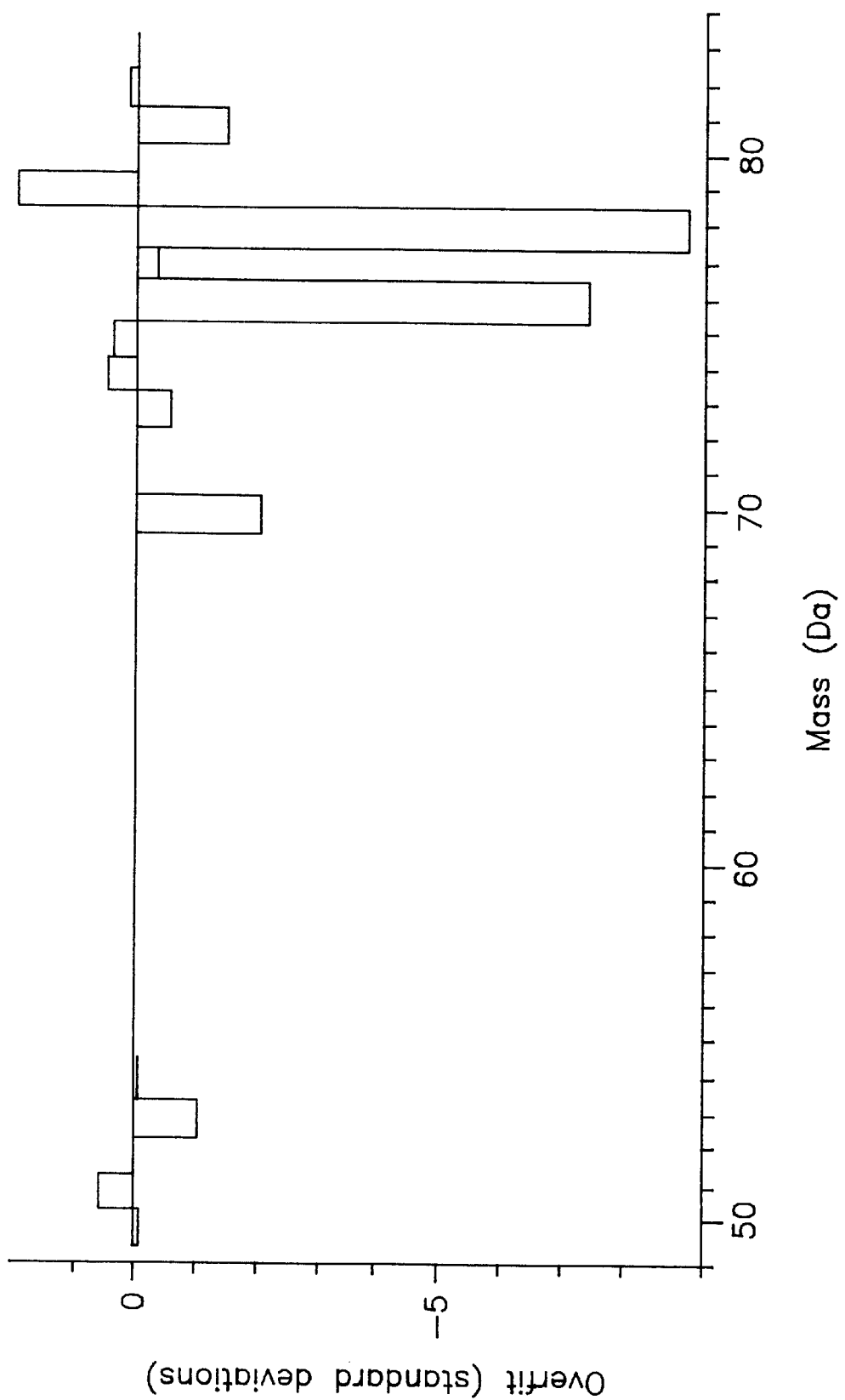
Figure 5:
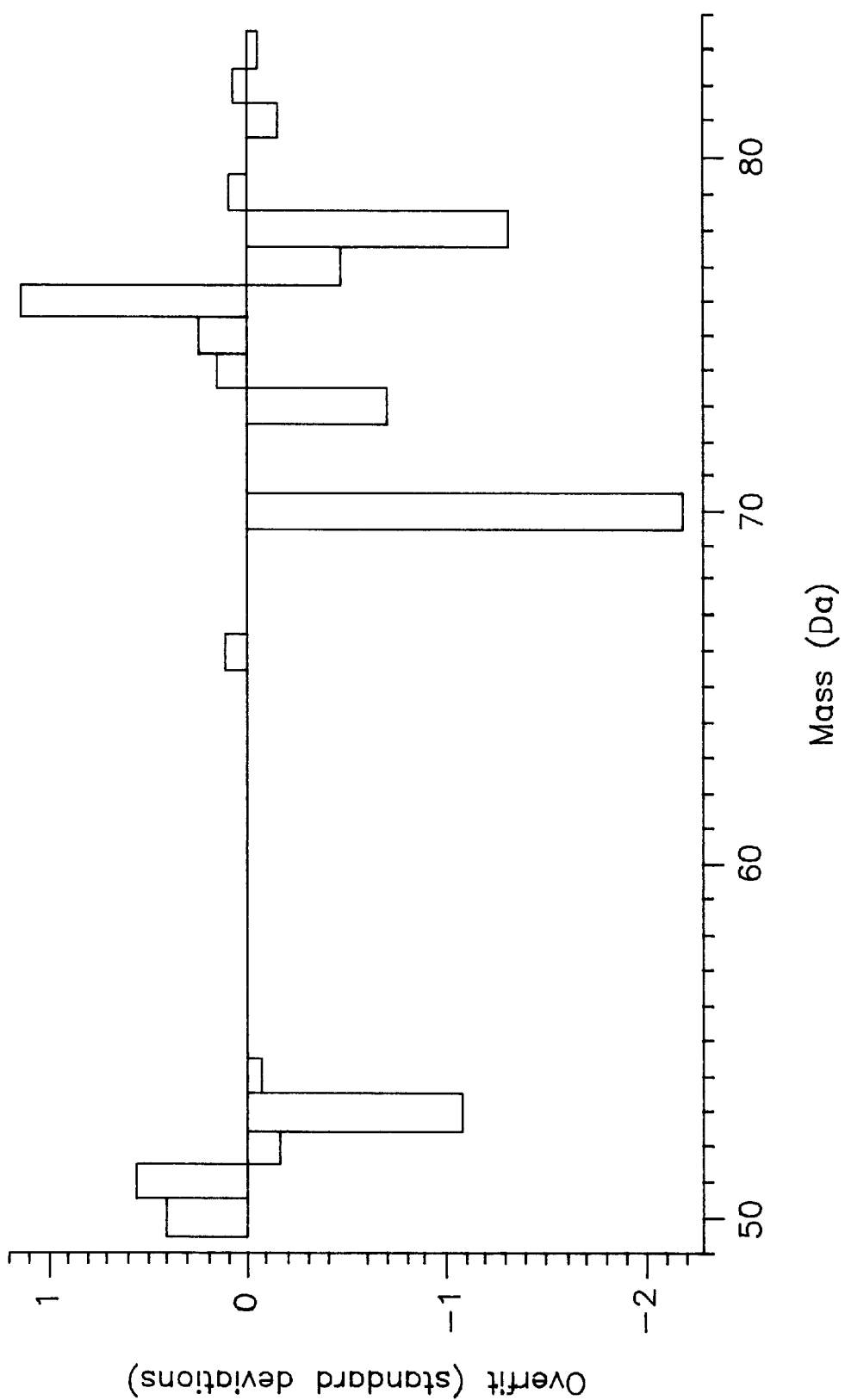

FIGS. 3–5 are "overfit" plots, each of which shows the difference in terms of standard deviations between the calculated signal at each particular mass corresponding to a particular list of possible constituents, and the experimental value. In FIG. 3, the list of possible constituents is Cr, Fe, Zn, Ge, Br and Kr. As can be seen, some of the differences between the trial and experimental values are highly significant, for example a difference of about 32 standard deviations at mass 51. The differences are highly statistically significant, and show that the list of possible constituents is very probably incorrect.

FIG. 4 shows a similar plot corresponding to the additional constituents ClO and ArCl. The operator has selected these constituents since their masses correspond to the underfits of the first attempt. Note that although FIG. 4 shows a better fit, there are still significant differences at masses 76 and 78. This would suggest the presence of diargon ($Ar_2$), amongst possible other constituents.

FIG. 5 shows a similar plot corresponding to the constituents of FIG. 4 plus the additional constituents ArN, $Ar_2$ and $Ar_2H$. The largest underfit is now just over 2 standard deviations at mass 70. This may be due to, for example, FeN, but essentially all the data is fitted to within the expected statistical parameters.

Figure 6:
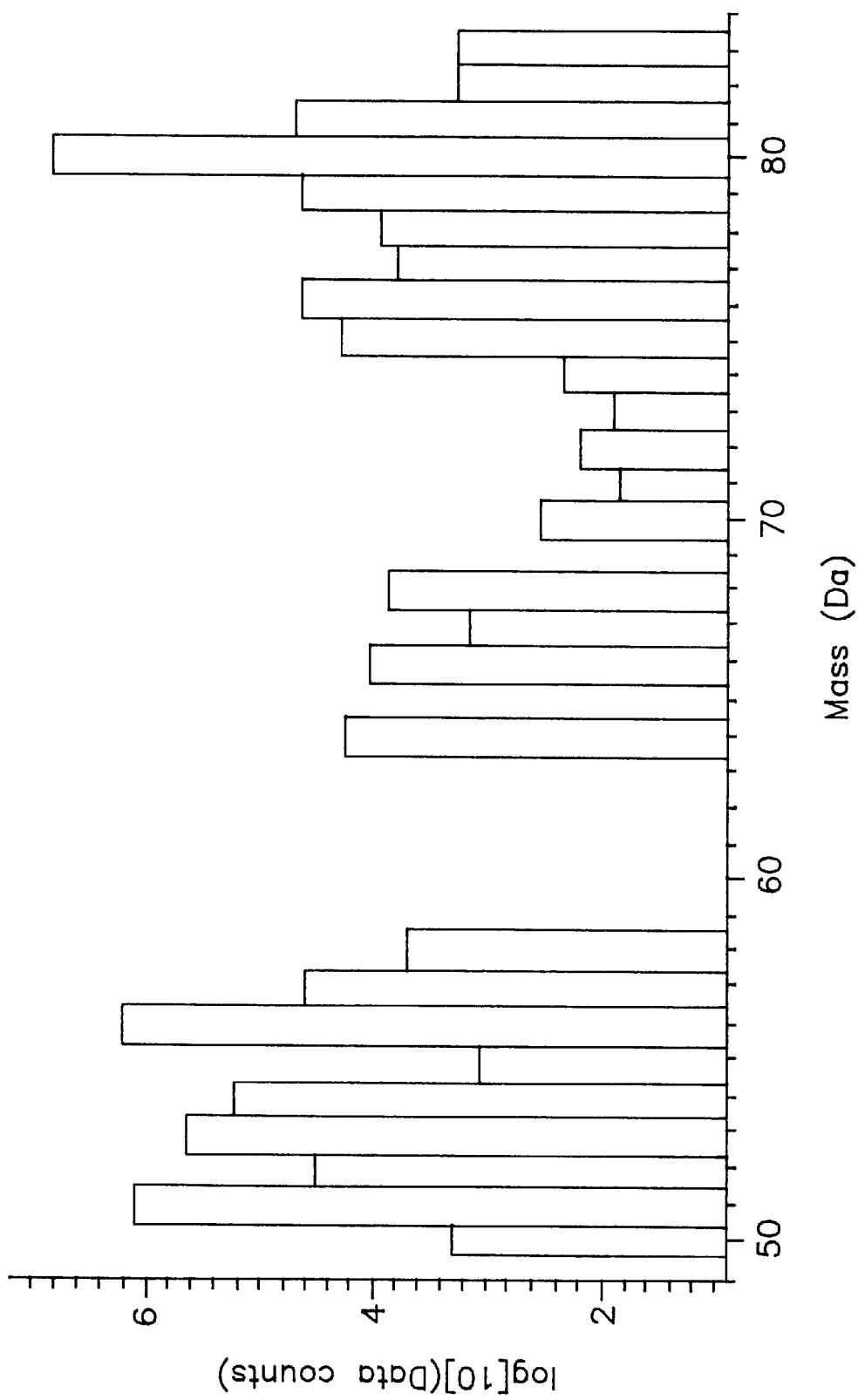
FIG. 6 is a mock or trial spectrum generated using the data obtained by the method of the invention.

FIG. 6 shows the "mock" mass spectrum which would be expected if the constitution of the sample actually does correspond to that which was used in calculating FIG. 5. FIG. 6 compares well with the actual data of FIG. 2 at all the x-values for which the mass was monitored, and furthermore the method is able to predict the data that would have been observed at the unmonitored masses had they been monitored.

I claim:

1. A method of determining the elemental composition of a sample by mass spectrometry comprising the steps of:
   i. introducing the sample to be analysed into the ionisation region of a mass spectrometer, the instrumental responsivity of which is known;
   ii. ionising the said sample so as to produce ions characteristic of the elements present therein;
   iii. mass analysing and detecting the said ions so as to obtain an experimental spectrum consisting of data counts observed at different values of mass-to-charge ratio characterised in that the method further comprises the steps of:
   a. generating a list of possible constituents of the sample, each said constituent having a known isotope ratio pattern;
   b. assigning a prior probability distribution to the said list of possible constituents;
   c. defining a set of trial compositions corresponding to the results of steps a and b;
   d. using the isotope ratio patterns together with the said instrumental responsivity to define a trial mass spectrum corresponding to each said trial composition;
   e. defining a posterior probability distribution by using probability calculus to compare the said trial mass spectra and the said experimental mass spectrum;
   f. generating a number of trial sets of possible compositions of the sample with their associated likelihood, which said trial sets are consistent with the said posterior probability distribution; and
   g. using the said trial sets and associated likelihoods to obtain mean values for the amount of each said constituent of the sample, together with corresponding associated uncertainties.

2. A method according to claim 1 wherein step a above involves the step of obtaining from the human operator of the mass spectrometer an estimate of the likely constituents of the sample.

3. A method according to claim 2 in which step a above involves displaying a menu of possible elements and/or species and allowing the operator to select the constituents which he or she estimates are present.

4. A method according to claim 3 in which the step of generating trial sets comprises the application of Gibbs sampling.

5. A method according to claim 4 further including the step of allowing the operator of the mass spectrometer to enter a revised estimate of the likely constituents depending on the result of the first or a prior calculation of the mean values for the amount of each constituent of the sample.

6. A method according to claim 3 further including the step of allowing the operator of the mass spectrometer to enter a revised estimate of the likely constituents depending on the result of the first or a prior calculation of the mean values for the amount of each constituent of the sample.

7. A method according to claim 2 in which the step of generating trial sets comprises the application of Gibbs sampling.

8. A method according to claim 7 further including the step of allowing the operator of the mass spectrometer to enter a revised estimate of the likely constituents depending on the result of the first or a prior calculation of the mean values for the amount of each constituent of the sample.

9. A method according to claim 2 further including the step of allowing the operator of the mass spectrometer to enter a revised estimate of the likely constituents depending on the result of the first or a prior calculation of the mean values for the amount of each constituent of the sample.

10. A method according to claim 1 in which step a takes place automatically.

11. A method according to claim 1 in which the trial sets generated in step f above are generated using Gibbs sampling.

12. A method according to claim 1 further including the step of allowing the operator of the mass spectrometer to enter a revised estimate of the likely constituents depending on the result of the first or a prior calculation.

13. A mass spectrometer operated according to the method of claim 1.

14. A mass spectrometer for determining the elemental composition of a sample by mass spectrometry, the instrumental responsivity of the mass spectrometer being known, the mass spectrometer comprising:

means for ionising the sample to be analysed so as to produce ions characteristic of the elements present therein;

means for mass analysing and detecting the said ions so as to obtain an experimental spectrum consisting of data counts observed at different values of mass-to-charge ratio characterised in that the mass spectrometer further comprises:

a. first generating means for generating a list of possible constituents of the sample, each said constituent having a known isotope ratio pattern;

b. assigning means for assigning a prior probability distribution to the said list of possible constituents;

c. defining means for defining a set of trial compositions corresponding to the results of the generating means and the assigning means;

d. means for using the isotope ratio patterns together with the said instrumental responsivity to define a trial mass spectrum corresponding to each said trial composition;

e. means for defining a posterior probability distribution by using probability calculus to compare the said trial mass spectra and the said experimental mass spectrum;

f. second generating means for generating a number of trial sets of possible compositions of the sample with their associated likelihood, which said trial sets are consistent with the said posterior probability distribution; and g. means for using the said trial sets and associated likelihoods to obtain mean values for the amount of each said constituent of the sample, together with corresponding associated uncertainties.

15. A mass spectrometer according to claim 14 in which the first generating means comprises means for obtaining from the human operator of the mass spectrometer an estimate of the likely constituents of the sample.

16. A mass spectrometer according to claim 15 wherein the first generating means comprises means for displaying a menu of possible elements and/or species and allowing the operator to select the constituents which he or she estimates are present.

17. A mass spectrometer according to claim 14 including an automatic first generating means.

18. A mass spectrometer according to claim 14 wherein the second generating means comprises means for generating the trial sets using Gibbs sampling.

19. A mass spectrometer according to claims 14 to 18 further comprising means for allowing the operator of the mass spectrometer to enter a revised estimate of the likely constituents depending on the result of the first or a prior calculation.

20. A mass spectrometer according to claim 14 further comprising means for introducing the sample into the ionisation region of the mass spectrometer.

* * * * *

UNITED STATES PATENT AND TRADEMARK OFFICE
CERTIFICATE OF CORRECTION

PATENT NO. : 5,910,655
DATED : June 8, 1999
INVENTOR(S) : John Skilling

It is certified that error appears in the above-identified patent and that said Letters Patent is hereby corrected as shown below:

Claim 19, column 8, line 40, delete "claims 14 to 18" and insert --claim 14--.

Signed and Sealed this

Sixth Day of February, 2001

Attest:

Q. TODD DICKINSON

Attesting Officer

Director of Patents and Trademarks